United States Patent [19]
Sih

[11] 3,972,916
[45] Aug. 3, 1976

[54] DL-STRIGOL INTERMEDIATE
[75] Inventor: Charles J. Sih, Madison, Wis.
[73] Assignee: Wisconsin Alumni Research Foundation, Madison, Wis.
[22] Filed: Dec. 13, 1974
[21] Appl. No.: 532,759

Related U.S. Application Data
[62] Division of Ser. No. 450,950, March 13, 1974, Pat. No. 3,887,547.

[52] U.S. Cl. ............................................. 260/514 G
[51] Int. Cl.$^2$ ......................................... C07C 61/38
[58] Field of Search ................................. 260/514 G

[56] References Cited
UNITED STATES PATENTS
3,887,547   6/1975   Sih ...................................... 260/240

Primary Examiner—Robert Gerstl
Attorney, Agent, or Firm—Howard W. Bremer

[57] ABSTRACT

A process for preparing dl-strigol, a potent seed germination agent, which comprises preparing the 2-bromomethyl-substituted methyl ester of 2,6,6-trimethylcyclohex-1-en-3-one-1-carboxylic acid, alkylating and cyclizing the said compound with an excess of dimethyl sodiomalonate to obtain methyl 1,4-diketo-7,7-dimethyl-4,5,6,7-tetrahydroindane-2-carboxylate and its enol, subjecting the said keto and enol forms of the compound, in admixture, to alkylation with methyl bromoacetate followed by acidic hydrolysis and spontaneous decarboxylation to obtain methyl 1,4-diketo-7,7-dimethyl-4,5,6,7-tetrahydroindane-2-acetic acid, reducing the said acetic with a hydride reducing agent and recovering and separating the resulting 1,4-cis and trans-dihydroxy-7,7-dimethyl-4,5,6,7-tetrahydroindane-2-acetic acid lactones, formylating each of the cis and trans γ lactones, alkylating the respective resulting hydroxy methylene lactones with bromobutenolide and recovering dl-strigol, dl-4′-epi-strigol, dl-4-epi-strigol and dl-4,4′-diepi-strigol.

New compounds useful as intermediates in the above process are also shown.

1 Claim, No Drawings

DL-STRIGOL INTERMEDIATE

The invention described herein was made in the course of work under a grant or award from the Department of Health, Education, and Welfare.

This is a division of application Ser. No. 450,950, filed Mar. 13, 1974 now U.S. Pat. No. 3,887,547.

This invention relates to a process for the total synthesis of dl-strigol and to certain new compounds which are key intermediates in such process.

Strigol is a highly potent seed germination stimulant for the parasitic witchweed (Striga lutea Lour). This compound was first isolated from the root exudates of cotton in 1966 (C. E. Cook et al, Science 154, 1189 (1966)) but its structure and relative configuration have only recently been derived (C. E. Cook et al, J. Amer. Chem. Soc. 94, 6198 (1972)). Although it is known that strigol is an extremely active compound, concentrations of $10^{-14}$ M to $10^{-16}$ M being capable of stimulating seed germination, its availability from natural sources has been insufficient for the conduction of biological studies.

The primary purpose of this invention is to provide a process for the total synthesis of dl-strigol and thereby make the compound readily available in quantities sufficient for both investigative and commercial purposes.

A prime commercial application for strigol lies in control of witchweed, a root parasite plant which is found in many countries of the world and which, if uncontrolled, can have a disasterous effect on available food supplied since it parasitizes important food and forage crops.

Witchweed does not generally germinate until stimulated by a chemical stimulant secreted by the roots of certain plants. This stimulant has been identified as strigol. It is speculated that strigol can be used effectively as a witchweed control agent by applying it to soil containing witchweed seeds thereby stimulating their germination in the absence of a crop plant and then killing the witchweed before germination of the crop plant occurs. Hence strigol can readily become an extremely valuable agricultural chemical.

The process for producing dl-strigol in accordance with the present invention is fully set forth in the following schematic presentation and detailed description. Identical compounds are identified by like numbers in the schematic diagram and in the detailed description following the schematic. It is to be particularly noted that alternative pathways can be used to obtain compound 4 which is identified as methyl 2-(bromomethyl)-6,6-dimethyl-2-cyclohexen-3-one-1-carboxylate. Also, for the sake of clarity, in the detailed description each of the reactions described has been shown schematically in relation to that particular reaction.

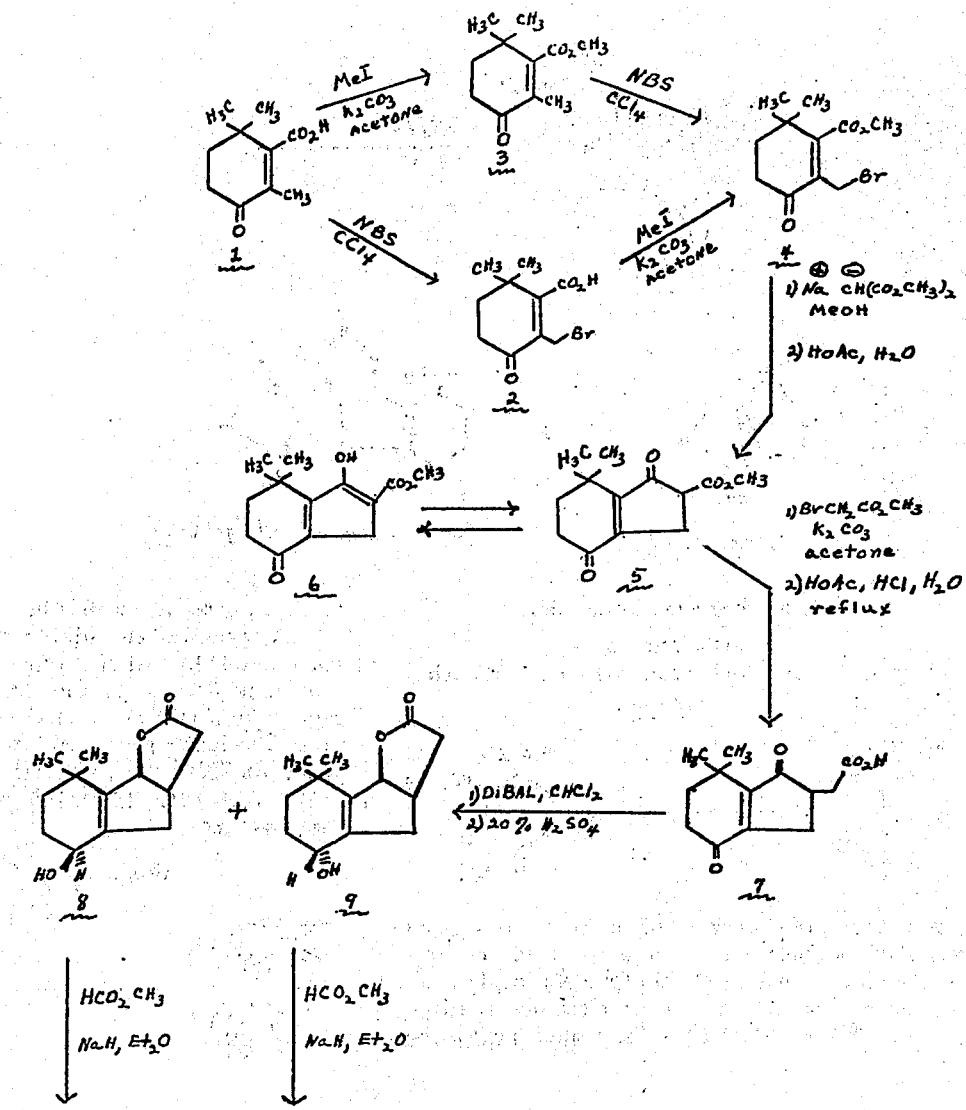

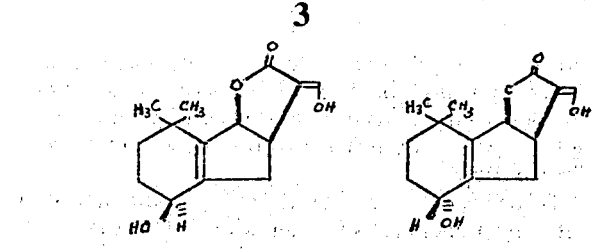

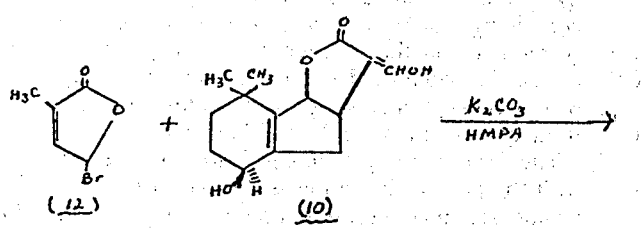

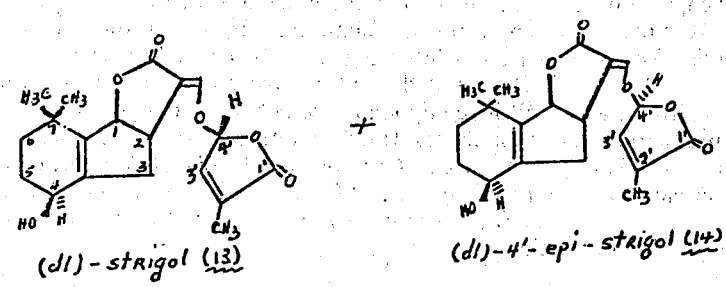

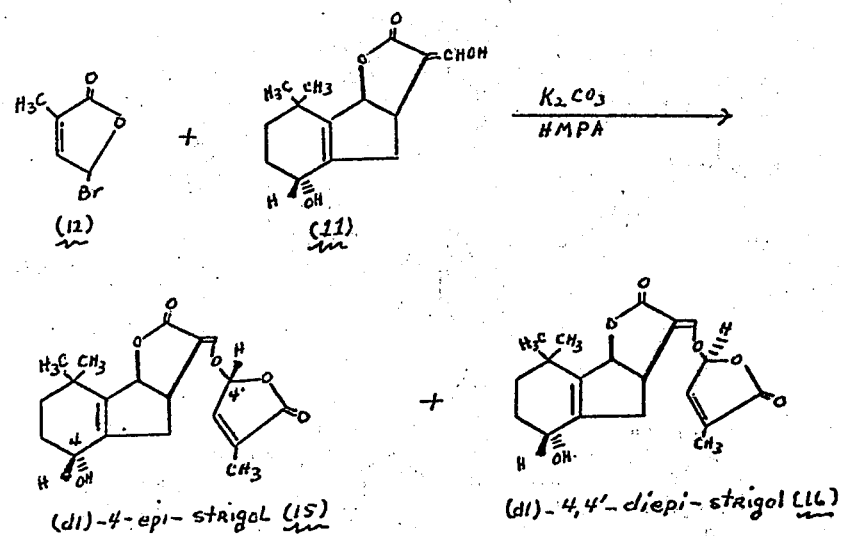

Detailed Process Description

Methylation of 3-oxo-2,6,6-trimethyl-cyclohex-1-en-1-Carboxylic Acid (1)

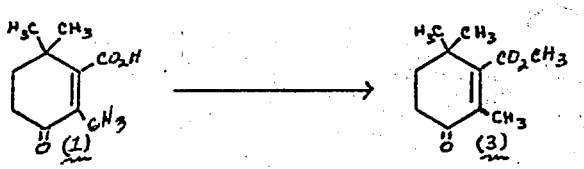

A mixture of 114 g (0.63 mol) of 3-oxo-2,6,6-trimethyl cyclohex-1-en-1-carboxylic acid, 114 g of potassium carbonate, 120 ml of methyl iodide, and 1 liter of mixture was then concentrated under reduced pressure. Water was added to the residue and the mixture was extracted with ether. The combined ether extracts were washed with water and saturated sodium chloride solution. After drying over anhydrous sodium sulfate, the solvent was evaporated to give 122 g methyl ester, (3) of satisfactory purity for further transformation. Distillation gave pure material (121 g. 98.5% yield); bp 72.5°–74.5°/0.02 mm; ir (film) 1727, 1678, 1620, 1430, 1312, 1236, 1053, 1018, 930, 867, 840, 799, 743 cm$^{-1}$.

Bromination of —(3)

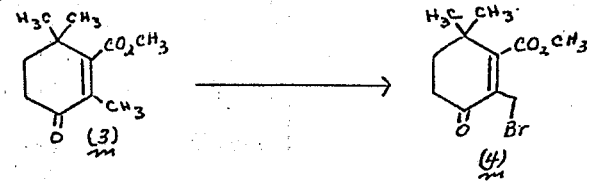

A mixture of 122 g (0.62 mol) of crude keto ester (3), 133 g of N-bromosuccinimide, and 700 ml of carbontetrachloride was refluxed under $N_2$ for 1 hr. with illumination under a 125-W tungsten lamp. After this period, the reaction was judged complete by the floating succinimide. The cooled reaction mixture was filtered and concentrated to give 172 g (100%) of crude bromide, (4), as a yellow oil which was suitable for subsequent reactions without further purification. Vacuum distillation (0.15 mm, bath temperature 98°–100°C) gave pure material: ir (film) 1728, 1684, 1613, 1430, 1245, 1150, 1118, 1082, 1025, 982, 878, 820, 798 cm$^{-1}$.

Alternatively the bromination of 3-oxo-2,6,6-trimethyl-cyclohex-1-en-1-carboxylic acid can be carried out first followed by the methylation as follows:

Bromination of
3-oxo-2,6,6-trimethylcyclohex-1-en-1-Carboxylic Acid
(1)

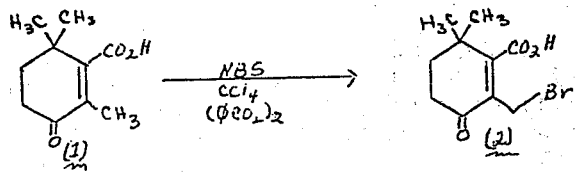

A mixture of 2.01 g of N-bromosuccinimide, 1.84 g of 3-oxo-2,6,6-trimethylcyclohex-1-en-1-carboxylic acid (1), and ca. 20 mg of benzoylperoxide in 150 ml of carbon tetrachloride was stirred and heated with reflux under nitrogen for 0.5 hr. at which time the reaction was judged complete by the floating succinimide. The reaction mixture was cooled, diluted with ether and washed with three portions of water. The organic layer was dried over anhydrous sodium sulfate and concentrated under reduced pressure to give 2.52 g (95%) of crude solid product. Recrystallization from chloroform afforded pure bromo acid (2); mp 181°–183°C; nmr (acetone-d$_6$) δ1.34 (6, s), ca. 2.0(2,m, masked by acetone peaks), 2.45–2.74 2,m), 4.22(2,s).

Methylation of the bromo acid (2) can be readily carried out in accordance with the methylation procedure set forth above.

Methyl
1,4-Diketo-7,7-dimethyl-4,5,6,7-tetrahydroindane-2-carboxylate (5) and enol (6)

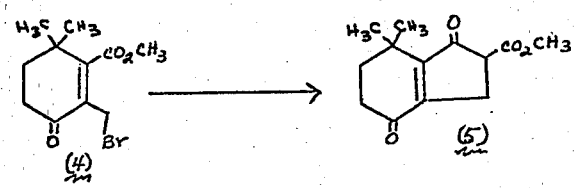

To a solution of 92 g (1.7 mol) of sodium methoxide (MCB) in 850 ml of methanol, stirred at room temperature under nitrogen, was added 238 g (1.8 mol) of dimethyl malonate. The mixture was cooled in an ice water bath to 5°C and was maintained at this temperature as a solution of 116.5 g (0.42 mol) of methyl 2-(bromomethyl)-6,6-dimethyl-2-cyclohexen-3-one-1-carboxylate (4) and 200 ml of methanol was added dropwise. After the addition was complete (ca. 1 hr.), the cooling bath was removed, and the mixture was stirred under nitrogen at room temperature for 24 hr. The reaction mixture was then refluxed under nitrogen for 6 hrs. to ensure complete reaction. After cooling in an ice bath, the reaction mixture was neutralized by dropwise addition of acetic acid. The mixture was poured into water and extracted with 3 portions of benzene. The combined benzene extracts were washed with water (twice), saturated NaHCO$_3$ (twice), water (4 times), and saturated NaCl. The benzene extracts were dried (anh. Na$_2$SO$_4$) and evaporated under reduced pressure removing some of the excess dimethyl malonate. The partially solidified residue was crystallized from ethyl acetate to give 86.23 g (86%) of β-ketoester (5) (mp 150°–154°C). The isolated solids varied from run to run in the relative amounts of the keto and enol forms judging by the nmr spectra, although the latter usually predominated. This solid product was suitable for further transformations without additional purification. A sample containing nearly all enol (6) had the following spectral characteristics: ir (KBr) 3250, 2940, 2850, 1690, 1658, 1604, 1540, 1436, 1385, 1375, 1298, 1263, 1222, 1190, 1095, 1050, 973, 830, 764 cm$^{-1}$; nmr (CDCl$_3$) δ1.42 (6,s), 1.85–2.11 (2,m)2.43–2.68(2,m), 3.30 (2,s), 3.86 (3,s), 10.3 1, bs).

(+)
14-Diketo-7,7-dimethyl-4,5,6,7-tetrahydroindane-2-Acetic Acid (7)

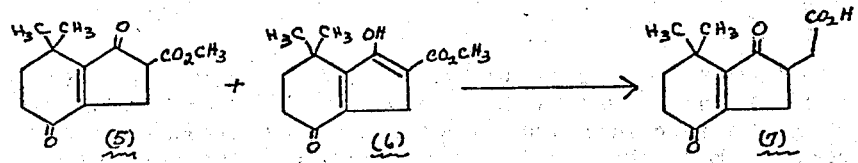

To a solution of 21.3 g (0.09 mol) of the β-ketoester (5 and 6) (containing varying amounts of keto and enol forms) in 400 ml THF, stirred under N$_2$ at ambient temperature, was added 26.0 g of anhydrous potassium carbonate followed by 25 ml of methyl bromoacetate. The mixture was stirred under N$_2$ for 48 hr. at which point the reaction was judged to be complete by tlc examination (Al$_2$O$_3$ plates; CHCl$_3$-acetone, 8:2). The mixture was diluted with water and extracted with three portions of ether. The ether extracts were washed successively with water, saturated NaHCO$_3$ solution, and water (twice). After concentrating under reduced pressure, the residue (29.1 g) was dissolved in a solution of 350 ml of glacial acetic acid and 350 ml of 6 N HCl. The solution was placed under a N$_2$ atmosphere and was heated to boiling with slow distillation for 3 hr. The dark reaction mixture was cooled, diluted with water, and extracted with ethyl acetate several times. The combined ethyl acetate extracts were washed with water and saturated sodium chloride solution. The dried (sodium sulfate) extracts were concentrated, and the residue was crystallized from benzene to give 12.75 g (mp 136°–137° C) of diketo acid (7). A second crop of 2.63 g (mp 135°–136° C) was obtained from the mother liquors for a total yield of 72%. Recrystallization from benzene afforded pure material: mp 136.5°–137° C; ir (KBr) 3600–2800, 1737, 1695, 1657, 1290, 1204, 1157 cm$^{-1}$; uv max (95% $C_2H_5OH$) 260 nm ($\epsilon$ 13,300); nmr ($CDCl_3$)$\delta$1.33 (6,s), 1.84–2.2 (2,m), 2.4–3.3 (7,m), 10.6(1,bs).

Treatment of the acid (7) with ethereal diazomethane gave the corresponding methyl ester as an oil: ir (film) 1735, 1705, 1685, 1436, 1360, 1215, 1167 cm$^{-1}$.

1α,4α-Dihydroxy-7,7-dimethyl-4,5,6,7-tetrahydroindane-2α- Acetic Acid γ-lactones (8 and 9)

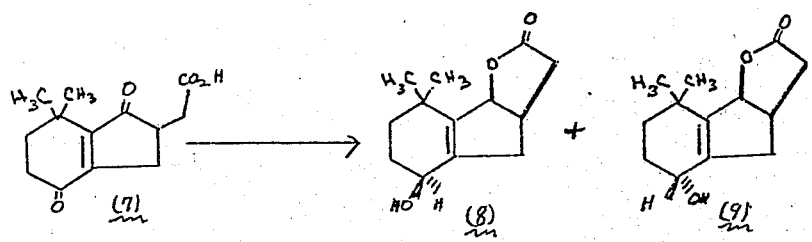

A solution of diisobutylaluminium hydride (DIBAL) (1.5M, 40.00 ml; 60 mmoles) in dry toluene was added (~5 min) to a mechanically stirred and cooled (dry ice-acetone bath) solution of diketo acid (7) (3.54 g; 15 mmoles) in dry dichloro methane (200 ml) under nitrogen atmosphere. The mixture was stirred for 2 hr. The excess of reagent was quenched with 20% of sulfuric acid (100 ml), and diluted with water (100 ml). Dichloromethane layer was separated and the aqueous portion extracted with dichloromethane. Combined extract was washed with water, brine and dried over anhydrous $Na_2SO_4$. Solvent was removed on rotary evaporator to give 3.246 g of the product. Chromatography on silica gel gave 2.005 g (60.2%) of a mixture of hydroxy lactones (8 and 9). Lactones (8) and (9) were separated on neutral alumina (Woelm; activity III) in a ratio of ca 2:1. Slow moving hydroxy lactone (8) was crystallized from benzene (m.p. 143–144); nmr ($CDCl_3$) δ 1.08 (3,s) 1.14 (3,s), 1.4–3.0 (9, complex), 4.12 (1, t, J = 5 Hz), 548 (1,d,J = 6.8 Hz); ir $CHCl_3$) 3600 and 3480 (OH), 1764 cm$^{-1}$(lactone>c=o). The faster moving hydroxy lactone (9) was obtained as an oil: nmr ($CDCl_3$)$\delta$1.09 (3,s), 1.13 (3,s),1.4–3.0 (9, complex), 4.18 (1,t,J = 4.9 Hz), 5.49 (1,d,J = 5.4 Hz); ir ($CHCl_3$) 3600 (OH), 1760 cm$^{-1}$ (lactone C=O).

Other hydride reducing agents such as diborane can be used in place of the DIBAL with like results.

Formylation of 1β, 4β-dihydroxy-7,7-dimethyl-2,3,5,6-tetrahydroindane-2β-acetic acidγ-lactone (8)

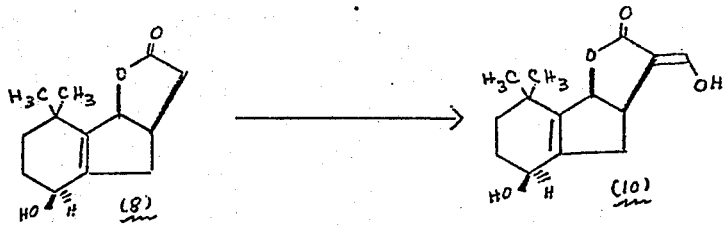

Methyl formate (0.7 ml) was added (~5 min) to a stirred mixture of sodium hydride (182 mg; 50% suspension in oil) and hydroxy lactone (8) (155 mg) in dry ether (20 ml), under $N_2$ atmosphere at room temperature (~25°). After 16 hrs. of stirring more of methyl formate (0.4 ml) was added to the reaction mixture and stirring continued for another 8 hrs. The mixture was made alkaline with 10% of sodium bicarbonate solution and extracted with ethylacetate. The alkaline portion was acidified and extracted with ethyl acetate. Extract from the acidic portion was washed with water, brine, dried ($Na_2SO_4$) and solvent removed on rotary evaporator to give 137 mg (78.5%) of hydroxy methylene lactone (crude (10) nmr (DMSOd6). δ7.41 (1,d,J.= 2. OHz) = CH—OH. As information given by its nmr was sufficient and the compound was used as such, without any purification, for the next reaction.

Formylation of 1β,4αdihydroxy-7,7-dimethyl-4,5,6,7-tetrahydroindane-2β acetic acid γ-lactone (9)

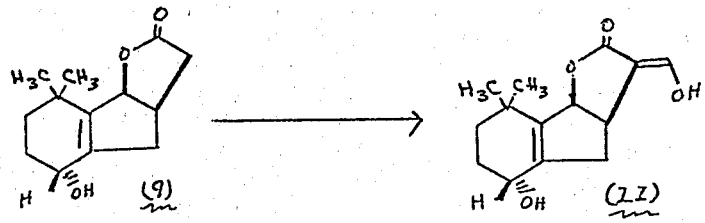

Methyl formate (0.5 ml) was added (~5 min) to a stirred mixture of sodium hydride (166 mg 50% suspension in oil) and hydroxylactone (9)(136 mg) in dry ether (10 ml) under N₂ atmosphere at room temperature (25°). Stirring was continued for ~18 hrs. Water was added to the reaction mixture and extracted with ethylacetate. The ethyl acetate extract was washed with water and brine and dried. Solvent was evaporated to give 133 mg of the product (11), nmr of the crude product in DMSO d6 shows the presence of hydroxy methylene proton signal. This compound was used as such for next step, without purification.

dl-Strigol (13) and dl-4'-epi Strigol (14)

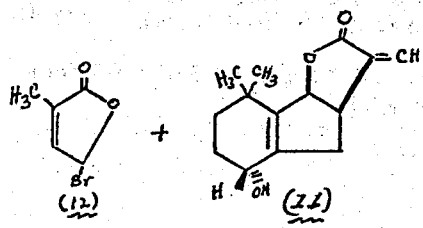

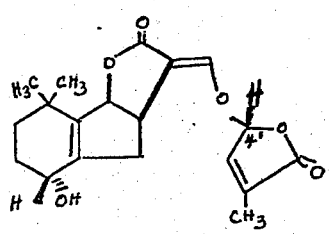

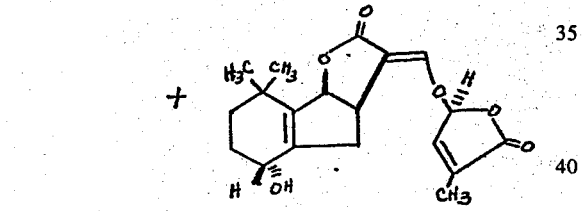

Bromobutenolide (12) (175 mg) was added to a stirred mixture of crude hydroxy methylene lactone (10) (137 mg), potassium carbonate (154 mg) and HMPA (5 ml). After 10 hrs. stirring more of bromobutenolide (12) (100 mg) was added to the reaction mixture and stirring continued for another 10 hrs. Water (10 ml) was added to the reaction mixture which was then extracted with ethyl acetate. The ethyl acetate extract was washed with water, brine and dried over anhydrous Na₂SO₄. Solvent was flashed off on a rotary evaporator giving 222 mg of the product. TLC showed presence of bromobutenolide and two more spots. This mixture was cleanly separated by preparative thin layer chromatography (silica gel; CHCl₃-acetone, 4:1) to give isomer A (14) ca. 25% yield Rf = 0.32, m.p. 178°-180° (ethyl acetate-hexane), m/e 346.1408, ir (CH₂Cl₂) 3590 cm⁻¹ (—OH), butenolide (1785, 1745 cm⁻¹) and 1682 cm⁻¹ (end ether, or unsaturated ketone) nmr: The geminal dimethyl groups (Ha) appear as singlets at δ 1.16 and 1.08, the four cyclohexane methylene protons (H_b) at 1.52 (br), and the vinylic methyl-(Hj) at 1.99 (t, J=1.5 Hz). The cyclopentane methylene hydrogens (δ 2.67) (Hd,d) are essentially equivalent, but are coupled to He (J=6 Hz). The latter resonance (δ3.61) is also coupled to Hf (δ5.48) (d, J=8 Hz) and allylically coupled to the highly deshielded proton Hg (δ7.42) (d,J=2.5 Hz). Protons H_h and Hi (δ6.89) are coupled to each other (J=1.5 Hz). A broad peak at δ4.90 is assigned to H_c (the allylic alcohol) isomer B (13) ca. 25% yield M/e 346 1408, Rf 0.20, m.p. 203°-205° (ethyl acetate-hexane) nmr and ir similar to isomer A.

(dl)-4-epi-Strigol (15) and (dl)-4,4'-diepi-Strigol (16)

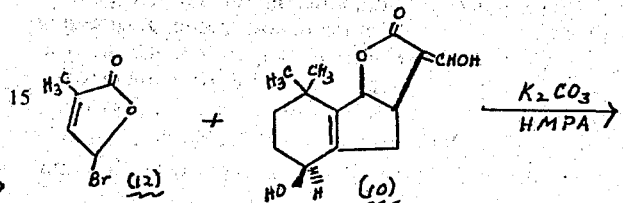

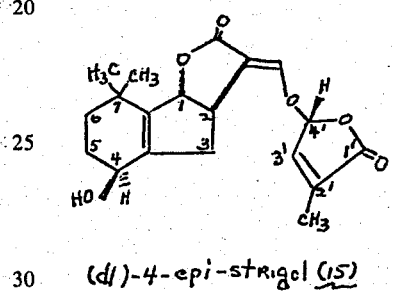

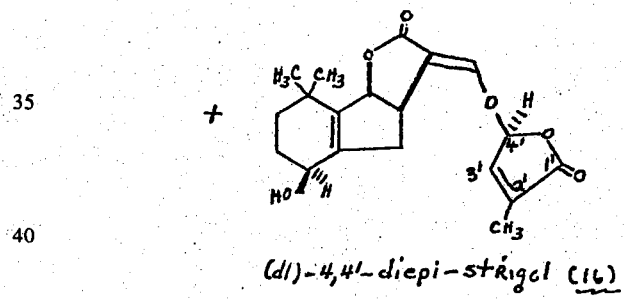

Bromobutenolide (12) (152 mg) was added to a stirred mixture of hydroxymethylene lactone (11) (133 mg; 0.532 mmole). Potassium carbonate (152 mg) and HMPA (~5 ml). After 18 hrs. of stirring, water (5 ml) was added to the product and extracted with ether. Ether extract was washed with water, brine and dried to give 84.5 g (46%) of the product. This product on chromatography gave 54 mg of mixture of (15) and 16). Mass spectrum of the mixture shows M⁺ at m/e 346, nmr is almost similar to strigol, except two methylene protons (Hd), which are shifted to higher field.

The bromobutenolide used in the foregoing reactions was prepared as follows:

4-Bromo-4-hydroxy-2-methyl-2-butenoic Acid Lactone (12)

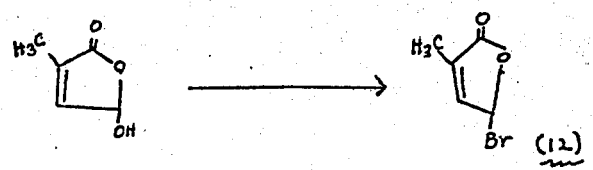

A solution of 3.09 g (27 mmole) of 4,4-dihydroxy-2-methyl-2-butenoic acid lactone (F. Farmia and M. V.

Martin, Annales de Quimica 67, (1971) and 11.2 g (34 mmole) of carbon tetrabromide in 35 ml of dry dichloromethane, stirred under nitrogen with cooling in an ice-water bath, was treated with a solution of 7.8 g (30 mmole) of triphenylphosphine in 20 ml dichloromethane by dropwise addition a period of 40 min. After stirring for an additional 5 hrs. at 0°, the liquid was decenated from the solid triphenylphosphine oxide which was rinsed twice with ether. The decanted liquid and other rinses were combined and chilled in an ice bath to crystallize out additional amounts of triphenylphosphine oxide. After again decanting and rinsing with ether, the solvents were evaporated, and the residue was distilled in vacuo to give the Bromobutenolide 12 (3.25 g, 68%: bp 54°/0.4 mm; ir (film 1778, 1650, 1435, 1318, 1206, 1080, 1033, 948, 860, 797, 754, 670 $cm^{-1}$; uv max (95% $C_2H_5OH$) 212 nm ($\epsilon$12,600; nmr (CDCl$_3$) 1.98 (3,t,J=1.64 Hz), 6.83 (1, pentet, J=1.6 Hz), 7.20 (1, pentet, J=1.6 Hz).

It is believed that certain of the compounds produced in the foregoing process are new and novel and have utility as key intermediates in the process. Specifically these compounds are those numbered 7, 8 and 9 in the above schematic of the process and are respectively:

7. (±) 1,4-diketo-7,7-dimethyl-4,5,6,7-tetrahydroindane-2-acetic acid;
8. (±) 1β, 4β-dihydroxy-7,7-dimethyl-4,5,6,7-tetrahydroindane-2β-acetic acid γ-lactone;
9. (±) 1β, 4α-dihydroxy-7,7-dimethyl-4,5,6,7-tetrahydroindane-2β-acetic acid γ-lactone.

Having thus described the invention what is claimed is:

1. (±) 1,4-diketo-7,7-dimethyl-4,5,6,7-tetrahydroindane-2-acetic acid (7).

* * * * *